US012788856B2

(12) United States Patent
Visciano et al.

(10) Patent No.: US 12,788,856 B2
(45) Date of Patent: Nov. 10, 2026

(54) PERITONEAL DIALYSIS CONCENTRATE POUCHES

(71) Applicant: Bellco SRL, Mirandola (IT)

(72) Inventors: Angela Visciano, Mirandola (IT); Guilherme Pagatini, Mirandola (IT); Genni Vesperini, Mirandola (IT); Marco Lupotti, Mirandola (IT)

(73) Assignee: Bellco S.R.L., Mirandola (IT)

( * ) Notice: Subject to any disclaimer, the term of this patent is extended or adjusted under 35 U.S.C. 154(b) by 929 days.

(21) Appl. No.: 18/018,436

(22) PCT Filed: Jul. 29, 2020

(86) PCT No.: PCT/IT2020/000059
§ 371 (c)(1),
(2) Date: Jan. 27, 2023

(87) PCT Pub. No.: WO2022/024148
PCT Pub. Date: Feb. 3, 2022

(65) Prior Publication Data
US 2023/0277739 A1 Sep. 7, 2023

(51) Int. Cl.
*A61M 1/16* (2006.01)
*A61M 1/28* (2006.01)
(Continued)

(52) U.S. Cl.
CPC ........ *A61M 1/1666* (2014.02); *A61M 1/1668* (2014.02); *A61M 1/167* (2014.02);
(Continued)

(58) Field of Classification Search
CPC .. A61M 1/287; A61M 1/1666; A61M 1/1668; A61M 1/167; A61M 1/28;
(Continued)

(56) References Cited

U.S. PATENT DOCUMENTS 3,166,020 A * 1/1965 Cook .................... B01F 25/312 417/198
3,826,474 A * 7/1974 Pareja .................. B01F 25/211 137/888
(Continued)

FOREIGN PATENT DOCUMENTS

AU 4160500 A * 10/2000 ............... A61L 2/04
CA 3062836 A1 * 11/2018 ........... A61J 1/2093
(Continued)

OTHER PUBLICATIONS

WO-2011015715-A1, English Language machine translation (Year: 2011).*
(Continued)

*Primary Examiner* — Wesley G Harris

(57) ABSTRACT

The disclosure relates to concentrate pouches for use in peritoneal dialysis. The pouches can contain a solid, liquid, or aqueous solution. Water can be added to the concentrate pouches to facilitate dissolution and mixing of dry powders and/or aqueous concentrates to generate a peritoneal dialysis fluid for use in peritoneal dialysis therapy. The concentrate pouches can include a venturi to assist dissolution of concentrates.

19 Claims, 8 Drawing Sheets

(51) Int. Cl.

| | |
|---|---|
| ***B01F 21/20*** | (2022.01) |
| ***B01F 23/451*** | (2022.01) |
| ***B01F 23/50*** | (2022.01) |
| ***B01F 25/312*** | (2022.01) |
| ***B01F 35/513*** | (2022.01) |
| *B01F 101/22* | (2022.01) |

(52) U.S. Cl.
CPC .............. *A61M 1/28* (2013.01); *A61M 1/287* (2013.01); *B01F 21/20* (2022.01); *B01F 23/451* (2022.01); *B01F 23/56* (2022.01); *B01F 25/31243* (2022.01); *B01F 35/513* (2022.01); *B01F 2101/22* (2022.01)

(58) Field of Classification Search
CPC ..... A61M 1/1656; B01F 21/20; B01F 23/451; B01F 23/56; B01F 25/31243; B01F 35/513; B01F 2101/22; A61J 1/10
See application file for complete search history.

(56) References Cited

U.S. PATENT DOCUMENTS

2004/0217057 A1 11/2004 Rovatti
2010/0154647 A1 6/2010 Skalski et al.
2012/0067968 A1* 3/2012 Brennan ........... B01F 25/31243 239/9

FOREIGN PATENT DOCUMENTS

| | | | | | | |
|---|---|---|---|---|---|---|
| EP | 3466460 | A1 | | 4/2019 | | |
| EP | 3903851 | A1 | | 11/2021 | | |
| WO | WO-8803403 | A1 | * | 5/1988 | ............ | A61J 1/2089 |
| WO | WO-2008136452 | A1 | * | 11/2008 | ................ | A61J 1/10 |
| WO | WO-2011015715 | A1 | * | 2/2011 | ............. | D21H 21/16 |

OTHER PUBLICATIONS

Communication pursuant to Article 94(3) EPC from counterpart European Application No. 20775728.7 dated Nov. 22, 2023, 5 pp.
International Preliminary Report on Patentability from International Application No. PCT/IT2020/000059 dated Jan. 31, 2023, 7 pp.
International Search Report and Written Opinion of International Application No. PCT/IT2020/000059 dated Apr. 9, 2021, 9 pp.
Response to Communication pursuant to Article 94(3) EPC dated Nov. 22, 2023, from counterpart European Application No. 20775728.7 filed Mar. 20, 2024, 9 pp.
Response to Communication Pursuant to Rules 161(1) and 162 EPC dated Mar. 7, 2023, from counterpart European Application No. 20775728.7, filed Aug. 30, 2023, 9 pp.

* cited by examiner

PERITONEAL DIALYSIS CONCENTRATE POUCHES

FIELD

The disclosure relates to concentrate pouches for use in peritoneal dialysis. The pouches can initially contain a solid, liquid, or aqueous solution. Water can be added to the concentrate pouches to generate concentrates containing constituent parts of a peritoneal dialysis fluid for use in peritoneal dialysis therapy. The concentrate pouches can induce a venturi effect to assist dissolution of concentrates.

BACKGROUND

The known peritoneal dialysis fluid generation systems and methods sometimes generate peritoneal dialysis fluid from premixed bags or ready-to-use bags of liquid concentrated forms of peritoneal dialysis fluid. The known systems and methods require a large amount of storage space to contain the liquid peritoneal dialysis fluid, and are generally incapable of generating peritoneal dialysis fluid from solid materials in single use containers. The known systems and methods cannot generate peritoneal dialysis fluid with solutes in a range of concentrations that can be varied independent of any other solutes. Although some known systems and methods rely on mechanical mixing or agitation to dissolve dry powder, the systems often fail to provide sufficient or adequate mixing. One known system uses a diffuser configured as a series of spaced bars extending radially from a central pipe on an interior floor of a compartment containing a dry powder concentrate. The diffuser is intended to create a turbulent flow to dissolve the dry powder in the compartment. Still other systems and methods use various tube arrangement to dissolve dry powder. In one arrangement, fluid exits from a top of a tube and flows downward to dissolve powder in a container. However, the known systems often fail to completely or adequately dissolve dry powders when generating a concentrate solution within certain conditions such as temperature and pressure. The known systems are also often expensive, not disposable, and cannot be customized. The known systems can also require long periods of time to sufficiently or adequately dissolve powders or solid materials.

As such, there is a need for systems and methods that can sufficiently dissolve dry powder concentrate or solid materials. The need extends to an effective system for adequately and timely dissolving dry powders in a container and/or sufficiently mixing liquid concentrates. The need includes dissolving dry powders within certain time periods. The need includes varying the concentrations of solutes in the peritoneal dialysis fluid independently of any other solutes by having a modular system of concentrate containers containing either dry power or liquid concentrates. The need includes a system of dry powder peritoneal dialysis constituent components that can be customized to fit a patient's individual prescription or therapy goals. There is a further need for systems and methods that allow generation and use of concentrates for peritoneal dialysis from solid or liquid materials. The need extends to an easy to use system for preparing a peritoneal dialysis fluid in an in-home setting. The need extends to a system for generating peritoneal dialysis fluid that minimizes shipping volumes and storage space for constituent components.

SUMMARY OF THE INVENTION

The first aspect of the invention relates to a concentrate pouch. In any embodiment, the concentrate pouch can include a fluid inlet positioned at a bottom portion of the pouch wherein the fluid inlet includes a venturi tube entering an interior of the concentrate pouch; the venturi tube can have a first section distal to the interior portion of the concentrate pouch, the first section having a first diameter, a second section distal to the first section and proximal to the interior portion of the concentrate pouch, the second section having a second diameter smaller than the first diameter, and a third section distal to the second section and extending inwardly into the interior of the concentrate pouch, the third section having a third diameter larger than the second diameter, and having an suction port at or about a floor of the interior of the concentrate pouch, the suction port exposing an interior of the venturi tube to the interior of the concentrate pouch.

In any embodiment, the concentrate pouch can contain a solid material.

In any embodiment, wherein the first diameter of the first section or the third diameter of the third section is about four times the second diameter of the second section.

In any embodiment, the concentrate pouch can be constructed from a flexible material.

In any embodiment, the concentrate pouch can be constructed from a flexible material and can be a stand up pouch In any embodiment, wherein the floor of the concentrate pouch inwardly tapers towards the fluid inlet.

In any embodiment, the venturi tube can extend upwardly from a bottom of the concentrate pouch towards a top of the concentrate pouch.

The features disclosed as being part of the first aspect of the invention can be in the first aspect of the invention, either alone or in combination, or follow any arrangement or permutation of any one or more of the described elements. Similarly, any features disclosed as being part of the second or third aspects of the invention can be in the first aspect of the invention, either alone or in combination, or follow any arrangement or permutation of any one or more of the described elements.

The second aspect of the invention is drawn to a system. In any embodiment, the system can include one or more of the concentrate pouches of the first aspect of the invention fluidly connected to a peritoneal dialysis fluid generation system; and a control system programmed to pump water into the one or more concentrate pouches to generate a concentrate; and to pump a concentrate from the one or more concentrate pouches into the peritoneal dialysis fluid generation flow path and into a mixing container.

In any embodiment, the system can include a water source fluidly connectable to the one or more concentrate pouches.

In any embodiment, the one or more concentrate pouches can include a concentrate pouch containing dextrose, icodextrin or polydextrin, a concentrate pouch containing magnesium, calcium and sodium lactate, and a concentrate pouch containing sodium bicarbonate and sodium chloride.

In any embodiment, the one or more concentrate pouches can include a concentrate pouch containing dextrose, icodextrin or polydextrin, a concentrate pouch containing magnesium and calcium, and a concentrate pouch containing sodium bicarbonate, sodium chloride, and sodium lactate.

In any embodiment, the one or more concentrate pouches can include a concentrate pouch containing dextrose, icodextrin or polydextrin, a concentrate pouch containing magnesium, calcium, and sodium lactate, and a concentrate pouch containing sodium chloride.

In any embodiment, the one or more concentrate pouches can include a concentrate pouch containing dextrose, icodextrin or polydextrin, a concentrate pouch containing magnesium and calcium, and a concentrate pouch containing sodium chloride and sodium lactate.

In any embodiment, at least one of the concentrate pouches can initially contain a solid substance.

In any embodiment, at least one of the concentrate pouches can initially contain a liquid or aqueous substance.

In any embodiment, the control system can be programmed to pump an amount of water into the one or more concentrate pouches to completely dissolve materials within the one or more concentrate pouches.

In any embodiment, at least one of the one or more concentrate pouches can be a stand up pouch.

The features disclosed as being part of the second aspect of the invention can be in the second aspect of the invention, either alone or in combination, or follow any arrangement or permutation of any one or more of the described elements. Similarly, any features disclosed as being part of the first or third aspects of the invention can be in the second aspect of the invention, either alone or in combination, or follow any arrangement or permutation of any one or more of the described elements.

The third aspect of the invention is drawn to a method. In any embodiment, the method can include the steps of pumping water into one or more concentrate pouches of the first aspect of the invention; dissolving a material within the one or more concentrate pouches to generate a concentrate in each of the one or more concentrate pouches; and pumping the concentrate out of each of the one or more concentrate pouches.

In any embodiment, the method can include the step of pumping the concentrate from each concentrate pouch to a mixing container.

In any embodiment, the one or more concentrate pouches can include a concentrate pouch containing dextrose, icodextrin or polydextrin, a concentrate pouch containing magnesium, calcium and sodium lactate, and a concentrate pouch containing sodium bicarbonate and sodium chloride.

In any embodiment, the one or more concentrate pouches can include a concentrate pouch containing dextrose, icodextrin, or polydextrin, a concentrate pouch containing magnesium and calcium, and a concentrate pouch containing sodium bicarbonate, sodium chloride, and sodium lactate.

In any embodiment, the one or more concentrate pouches can include a concentrate pouch containing dextrose, icodextrin or polydextrin, a concentrate pouch containing magnesium, calcium, and sodium lactate, and a concentrate pouch containing sodium chloride.

In any embodiment, the one or more concentrate pouches can include a concentrate pouch containing dextrose, icodextrin, or polydextrin, a concentrate pouch containing magnesium and calcium, and a concentrate pouch containing sodium chloride and sodium lactate.

The features disclosed as being part of the third aspect of the invention can be in any other part of the third aspect of the invention, either alone or in combination, or follow any arrangement or permutation of any one or more of the described elements. Similarly, any features disclosed as being part of the first or second aspect of the invention can be in the third aspect of the invention, either alone or in combination, or follow any arrangement or permutation of any one or more of the described elements.

BRIEF DESCRIPTION OF THE DRAWINGS

FIG. 1A is a perspective view of a cutaway showing one side of the concentrate pouch. FIG. 1B is an exterior side view of the concentrate pouch.

DETAILED DESCRIPTION

Figure 1A:
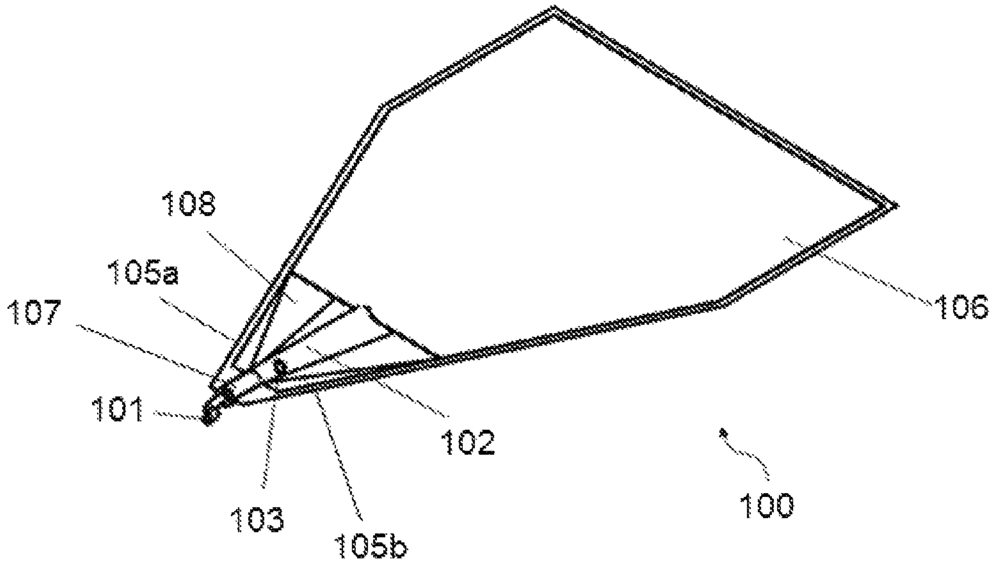
FIGS. 1A-B illustrate a concentrate pouch.

Unless defined otherwise, all technical and scientific terms used have the same meaning as commonly understood by one of ordinary skill in the art.

The articles "a" and "an" are used to refer to one to over one (i.e., to at least one) of the grammatical object of the article. For example, "an element" means one element or over one element.

The term "at least" refers to a possibility of one or more elements may be present. For example, a container containing at least magnesium provides for the possibility of containing one or more other components such as calcium.

The terms "aqueous," "aqueous substance," or an "aqueous solution" refer to a solution of a solute in water.

The term "bottom portion" refers to a surface or section nearest to a lowest point of the component or section when in an upright orientation.

The term "calcium," as used herein, can refer to any source of calcium, such as calcium chloride.

The term "completely dissolve" refers to the process of generating a solution from a solute in which essentially no solute remains undissolved.

The term "comprising" includes, but is not limited to, whatever follows the word "comprising." Use of the term indicates the listed elements are required or mandatory but that other elements are optional and may be present.

A "concentrate" refers to a solution of one or more solutes in water. The concentrate can have a solute concentration greater than that to be used in dialysis.

The term "concentrate pouch" refers to a container that can contains at any point in time any one or more of a solid such as powder, fluid, solutions, and any combination thereof. At a desired point, the concentrate pouch can contain a concentrate fluid to be formed or contained therein. The pouch can be made of any suitable material and can initially contain dry, wet, or a combination of dry and wet materials where the contents and state of the materials inside the container can change at any time.

The term "consisting of" includes and is limited to whatever follows the phrase "consisting of." The phrase indicates the limited elements are required or mandatory and that no other elements may be present.

The term "consisting essentially of" includes whatever follows the term "consisting essentially of" and additional elements, structures, acts or features that do not affect the basic operation of the apparatus, structure or method described.

The term "constriction" refers to any portion of a feature that is reduced in size, in reference to a compared feature such as for a tube, pipe, or flow path. For example, the constriction can have a smaller diameter relative in reference to a rounded tube or pipe. The constriction can mean any smaller opening relative to a section to which the constriction is being compared to, and is not limited to any specific relative size or shape. For example, a constriction can be flattened tube that has a smaller cross-sectional area of the flow path as compared to an adjoining tubular pipe that has a larger cross-sectional area of the flow path.

The term "constructed from" refers to a type of material that makes up a component.

The terms "contain" or "containing" refer to a material held within a component or container. The term contain is open ended and does not prevent the inclusion of other components being included within the same component.

The terms "control," "controlling," or "controls" can refer to the ability of one component to direct the actions of a second component.

A "control system" can be a device that monitors and affects the operational conditions of a given system. The operational conditions are typically referred to as output variables of the system wherein the output variables can be affected by adjusting certain input variables. The control system can any number or combination of processors, controllers, software, and computers.

The term "dextrose" refers to a simple sugar compound with a chemical formula $C_6H_{12}O_6$. Dextrose is the dextrorotatory form of glucose, and in certain embodiments, the terms dextrose and glucose can be used interchangeably.

The term "diameter" refers to a distance from one side of a circle to an opposite side of the circle through the center of the circle.

The term "dissolve" refers to the process of dissolution or more broadly, the generation of a solution from a solvent and solute.

The term "distal" refers to a section or component positioned away from a point of attachment or origin.

The term "downstream" refers to a position of a first component in a flow path relative to a second component wherein fluid will pass by the second component prior to the first component during normal operation. The first component can be said to be "downstream" of the second component, while the second component is "upstream" of the first component.

The term "exposing" in context of an suction port means allowing either side of the suction port having access to the other side of the opening or suction port.

The terms "extend" or "extending" refer to a portion of a component directed or situation in a specified direction or orientation.

The terms "first," "second," and "third," and the like, refer to separate and distinct features. For example, one or more sections can be identified as a 'first section," "second section," and "third section." Alternatively, one or more diameters can be identified as a 'first diameter," "second diameter," and "third diameter."

The term "flexible material" refers to a material that can change shape in response to applied pressure.

A "fluid path" of "fluid line" can refer to a tubing or conduit through which a fluid, gas, or a combination thereof can pass. The fluid path or line can also contain air during different modes of operation such as cleaning or purging of a path or line.

The term "fluidly connectable" refers to the ability to provide passage of fluid, gas, or combinations thereof, from one point to another point. The ability to provide such passage can be any mechanical connection, fastening, or forming between two points to permit the flow of fluid, gas, or combinations thereof. The two points can be within or between any one or more of compartments, modules, systems, components, all of any type. Notably, the components that are fluidly connectable, need not be a part of a structure. For example, an outlet "fluidly connectable" to a container does not require the container pump, but merely that the outlet has the features necessary for fluid connection to the container.

The term "fluidly connected" refers to a particular state or configuration of one or more components such that fluid, gas, or combination thereof, can flow from one point to another point. The connection state can also include an optional unconnected state or configuration, such that the two points are disconnected from each other to discontinue flow. It will be further understood that the two "fluidly connectable" points, as defined above, can form a "fluidly connected" state. The two points can be within or between any one or more of compartments, modules, systems, components, and rechargers, all of any type.

An "fluid inlet" is a portion of a component through which gas, fluid, and combinations thereof can enter or exit the component. Although the term inlet generally refers to an opening for entry of gas, fluid, and combinations thereof, the inlet can sometimes provide a means for exiting or exhausting the gas, fluid, and combinations thereof. For example, during a priming, cleaning, or disinfection, the inlet can be used to remove gas, fluid, and combinations thereof through the inlet. Also, during operation, the inlet can remove gas, fluid, and combinations thereof.

The terms "forming," "forms," and the like refers to any type of shape or structure of an object or feature.

The phrase "four times" refers to multiplying a value by four.

The phrase "generate a concentrate" or "generating a concentrate" refer to a process or steps for dissolving a solid or liquid material, or diluting a solution, to form a concentrated solution.

The term "icodextrin" refers to a water-soluble glucose polymer.

The terms "initial" or "initially" in reference to feature or object refers to a beginning or starting condition or state of the feature. For example, a "concentrate container initially containing a solid substance" refers to the container starting with a solid substance wherein a "subsequent" state or condition of the concentrate container can change, such as where a solid material is reconstituted by the addition of water. Similarly, the term "subsequent" refers to a following state or condition of the feature or object.

The term "interior" refers to an inside portion or section of an object or component. The term can also refer to a surface such as an interior wall of a tube, pouch, or container.

The term "inwardly tapering" describes a shape of a container or component that has a decreasing diameter, inclination, or size towards a location or point in a specified direction.

The term "liquid," "liquid substance," or a "liquid material" refer to a material in the liquid phase of matter.

The term "magnesium," as used herein, can refer to any source of magnesium, such as magnesium chloride.

A "mixing container" is a container into which one or more fluid streams can be flowed to generate a mixture. The mixing can occur by passive turbulence or active means such as an agitator.

An "opening" is a portion of a component that through which fluid or gas can enter or exit the component.

"Peritoneal dialysis fluid" is a dialysis solution to be used in peritoneal dialysis having specified parameters for purity and sterility. Peritoneal dialysate is not the same as dialysate used in hemodialysis.

"Peritoneal dialysis" is a therapy wherein a dialysate is infused into the peritoneal cavity, which serves as a natural dialyzer. In general, waste components diffuse from a patient's bloodstream across a peritoneal membrane into the dialysis solution via a concentration gradient. In general, excess fluid in the form of plasma water flows from a patient's bloodstream across a peritoneal membrane into the dialysis solution via an osmotic gradient. Once the infused peritoneal dialysis solution has captured sufficient amounts of the waste components the fluid is removed. This cycle can be repeated for several cycles each day or as needed.

A "peritoneal dialysis fluid generation flow path" is a fluid flow path that can receive fluids, concentrates, and/or water for the generation of a peritoneal dialysis fluid.

The term "positioned" refers to a component, feature, or process step connected to or in relation to the feature being referred to, or the relative location with respect thereto. The contact can be physical, fluid, temporal, or electrical and is intended to be used in the broadest reasonable sense.

The term "polydextrin" refers to any polymer formed from dextrose or glucose monomers.

The term "pouch" can refer to a flexible bag of any size and shape fabricated from a suitable material to hold any one of the concentrates of the invention.

The term "programmed" is to be interpreted in the broadest sense and can mean any series of instructions that cause a processor or a control system of any type including software to perform certain steps or to execute an algorithm of any type. For example, a processor can be programmed to execute an algorithm. Alternatively, a computer can be programmed to execute a series of functions of steps.

The term "proximal" refers to a section or component positioned nearest or adjacent to a point of attachment or origin.

The terms "pumping," "pumped," or to "pump" refer to moving or flowing a fluid using a pump of any type known to those of ordinary skill in the art.

The terms "pumping fluid" or to "pump fluid" refer to moving a fluid, gas, or a combination thereof through a flow path of any type with a pressure. The pressure can be generated by a pump of any type.

"Sodium bicarbonate" refers to $NaHCO_3$, either in solution or solid form.

"Sodium chloride" refers to NaCl, either in solution or solid form.

"Sodium lactate" refers to $C_3H_5NaO_3$, either in solution or solid form.

The terms "solid," "solid substance," or a "solid material" refer to a material in the solid phase of matter, and can include crystalline, powdered, or any other form of solid material.

The term "stand up pouch" refers to a concentrate pouch having a shape or components that will generally maintain the concentrate pouch in an erect position without support from other components.

The term "suction port" refers to an aperture or opening in a component or feature, commonly a tube or flow path, through which any material, fluid, gas, or combinations thereof can flow. Generally, flow is directed inwards through the suction port using any motive force such as a vacuum. However, the suction port is not constrained to inwardly directed flow wherein material, gas, or combinations thereof can flow outwards from the suction port under certain conditions.

The term "tube" refers to a conduit through which material, fluid, gas, or combinations thereof can flow.

The term "upwardly" refers to a direction from a bottom of a component towards the top of the component when the component is positioned for normal use.

The term "upright" refers to an orientation of a component that is the same vertical orientation as intended for use.

The term "venturi" as used in a "venturi tube," "venturi tube," "venturi effect," "venturi system," and the like, generally refer to a reduction in fluid pressure that results when a fluid flows through a constricted section of a flow path such as a tube.

The term "water source" refers to a source from which any one of potable, purified, or sterile water can be obtained.

Peritoneal Dialysis Pouches

FIG. 1A is a perspective cut-away of an interior side 106 of a peritoneal dialysis concentrate pouch 100. The concentrate pouch 100 can initially contain a solid or concentrated material of any type. The concentrate pouch 100 can contain any solid, liquid, aqueous solution, and combinations thereof in any state of mixing, partial dissolution, or complete dissolution. Upon dissolution and reconstitution of a solid such as powder, the solid contents of the pouch (not shown) can dissolve from a solid powder to a liquid solution, for example, by the addition of water. Fluid can be pumped into the concentrate pouch 100 through fluid tube 102, which can be fluidly connectable to a fluid line 101. The fluid line 101 can connect to a peritoneal dialysis fluid generation system (not shown) for generation of peritoneal dialysis fluid from the concentrate in concentrate pouch 100. The fluid tube 102 can extend upwardly into the concentrate pouch 100 and can include an integrated venturi feature of any type or configuration to induce a low-pressure zone after a constriction in the venturi. The low-pressure zone can be used to draw up material to dissolve solid material and form a solution within the concentrate pouch 104.

The integrated venturi feature or system of the invention can have at least one suction port 103 in fluid tube 102, as well as a constriction 107 in fluid tube 102 (not shown in FIGS. 1A-B) to create a low-pressure zone due to the venturi effect. The constriction 107 inside the venturi system of fluid tube 102 increases flow velocity and reduces pressure after the constriction 107. As fluid flow exits the constriction 107, a vacuum is created by the pressure drop as the fluid expands in a downstream section of fluid tube 102. The reduced pressure after the constriction 107 creates a vacuum such that material adjacent to a suction hole 103 is drawn into the fluid tube 102. The suction port 103 can be positioned at or about a floor of the interior of the concentrate pouch 100 to expose an interior of the fluid tube 102 to the interior of the concentrate pouch 100. The suction created by the venturi effect can draws in any material such as dry powder into suction port 103. The negative pressure at suction port 103 can draw in any dry powder or concentrate into the primary flow along the fluid tube 102. At the end of the fluid tube 102, a mixture of liquid and concentrate can appear without any separate mechanical agitation. The suction port 103 can be downstream of the constriction 107 at any suitable position on fluid tube 102. Additional suction ports anywhere from one or more suctions ports can be included in fluid tube 102. In one embodiment, up to six or more suction ports can be used. The suction ports can be exposed to an interior space inside the concentrate pouch 100. As such, material inside concentrate pouch 100 can be drawn in through the suction port 103 positioned in the low-pressure zone after the constriction 107 in the venturi. The fluid tube 102 can have a constant outer diameter while having diameters of varying size inside the venturi system of the fluid tube 102. The material can then travel upwardly for any length of the fluid tube 102 along with any fluid being flowed into the concentrate pouch 100. The combined fluid/material mixture can exit at a top of the fluid tube 102 inside the concentrate pouch 101.

Figure 1B:
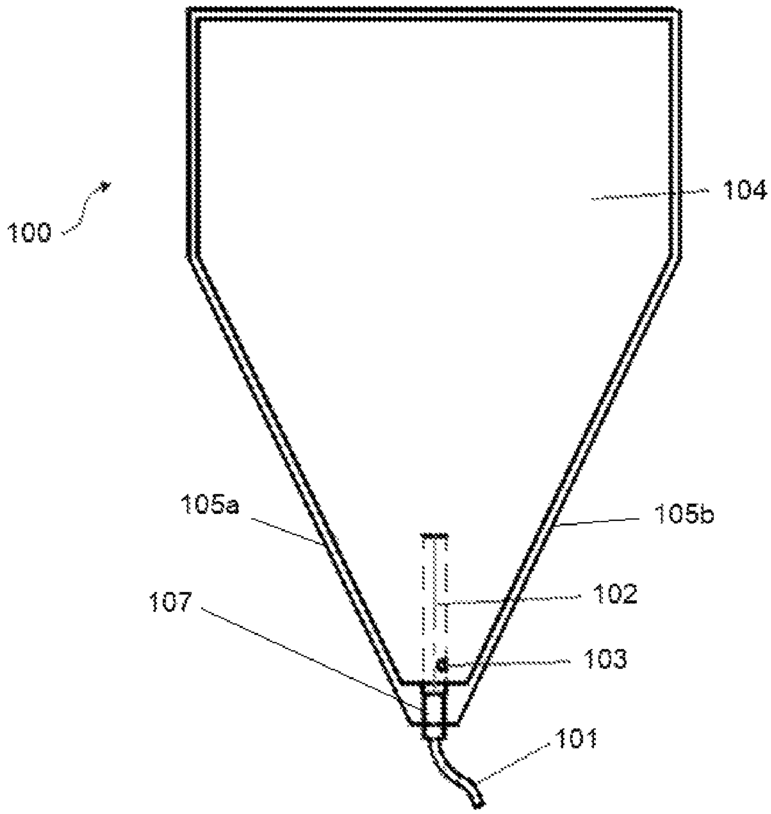

FIG. 1B is a side view of an exterior side 104 of the concentrate pouch 100. The fluid tube 102 can be positioned at or near a bottom portion of the concentrate pouch 100 in an upright position. The fluid tube 102 enters the interior of the concentrate pouch 100 at the bottom portion of the concentrate pouch 100. The fluid tube 102 can have a first section distal to the interior portion of the concentrate pouch 100 such that fluid flowing through the fluid tube 102 encounters the first section with a first diameter. Fluid can then flow into a second section defining the constriction 107 having a smaller diameter than the first section. Fluid can then flow into a third section having a third diameter larger than the second section. The first diameter can be larger than the constriction 107 in the second section or the diameter in the third section. Similarly, the diameter of the third section can be larger than one or both of the first and second section. The static pressure in the first section of the fluid tube 102 can be higher than at the second section downstream of the first section wherein any fluid speed in the first section is lower than in the second section due to a greater diameter in the first section relative to the second section.

The second section defining the constriction 107 can be proximal to the interior portion of the concentrate pouch 100 with respect to a third section of the fluid tube 102. The constriction 107 induces a higher fluid velocity but lower pressure. The diameter of the constriction 107 in the venturi system of the second section can be any suitable diameter relative to the first diameter sufficient to create a desired venturi effect or vacuum force in the third section. The third section of fluid tube 102 is distal to the second section and extends into the concentrate pouch 100 for any length In one embodiment, the fluid tube 102 extends to a top of the concentrate pouch 100. In another embodiment, the fluid tube 102 terminates at or near the suction port 103. As fluid exits the second section, a pressure drop is created in the third section and creates a vacuum that can suck up material adjacent to suction port 103. The third section has a third diameter larger than the constriction 107. The third section can create a turbulent flow and contain internal ridges or screw features (not shown) positioned along the length of an interior side of the fluid tube 102 to encourage mixture of materials suctioned into the fluid tube 102. By drawing material through the suction port 103 positioned at or near the bottom portion of the concentrate pouch 100, the materials can be mixed in the flowing fluid and more quickly dissolved. The mixture can then exit directly from the fluid tube 102 inside the concentrate pouch 100. The fluid/material mixture can then be flowed back through the suction port 103. Alternatively, the flow can reverse and mixed fluid, material, and/or solution can exit in the reverse direction through fluid tube 102. One or more pumps can reverse to provide the necessary motive force to draw the concentrate solution back through fluid tube 102.

The fluid tube 102 can extend any distance into the concentrate pouch 100. In certain embodiments, the fluid tube 102 can extend to a maximum of 10 mm into concentrate pouch 100. However, the fluid tube 102 can extend farther or shorter into the concentrate pouch 100, including distances greater than 10 mm. Dissolution can be unaffected over a range of sizes. As disclosed herein, any number of suction ports can be positioned in the low pressure region to draw in material into the flow path inside fluid tube 102. In certain embodiments, the inner walls of the pouch body 104 can include an inclination 105*a* and/or inclination 105*b*. In general, inclination 105*a* and inclination 105*b* can be an inwardly tapering of the inner walls of the pouch body 104 towards the fluid tube 102 at the bottom portion of the pouch body 104. The inclination 105*a* and inclination 105*b* can act to collect all materials including sold material, powders, partially dissolved concentrate, and/or fully dissolved concentrate at the bottom of the concentrate pouch 100. The collected materials and or solutions can be sucked through suction port 103 and dissolved or further mixed. Further, the inclination 105*a* and inclination 105*b* can help to avoid the creation of no-flow zones within the concentrate pouch 100. In certain embodiments, the inclination 105 of the inner walls can be between 20°-60°. In other embodiments, the bottom portion can be formed into a funnel to direct materials towards the suction port 103. Vertical ribs positioned on the interior side of the funnel can encourage materials and solutions to flow towards the bottom of the pouch body 104.

The fluid tube 102 can connect to fluid line 101 of a peritoneal dialysis generation system by any means known in the art. For example, the bottom of fluid tube 102 can include a capped and threaded portion that can mate with a threaded portion on a peritoneal dialysis system. Alternatively, the fluid tube 102 can include a rigid connector for connection to the peritoneal dialysis generation system. A flap (not shown in FIGS. 1A-B) can cover the rigid connector prior to connection to separate the contents of the concentrate pouch 100 from the outside environment. Alternatively, a peelable layer can be placed on the bottom of fluid tube 102 that can be removed prior to connection. The peelable layer can be formed from a polyolefin film or metal foil. The material can be made from any long-lasting, non-reactive material suitable for storage, sterility, and transport. The peelable layer can be made from any of a polymer selected from at least one of LLDPE (Linear Low Density Polyethylene), LDPE (Low Density Polyethylene) and HDPE (High Density Polyethylene), ethylene-vinyl acetate copolymer, ethylene-methyl acrylate copolymer and HDPE or any suitable material. The materials should form a consistent hermetic seal for leak protection and preserve the materials contained inside. The materials should provide tamper-evident protection but be sufficiently easy to open or peel.

The concentrate pouch 100 can be constructed from a flexible or rigid material, as desired. In certain embodiments, the concentrate pouch 100 can be made from mono or multilayer film material, including polypropylene-polyethylene or polypropylene-polyethylene-polyamide for multilayer polyolefin-based films; a monolayer polyolefin film such as polypropylene or polyethylene, or vinyl based films such as PVC or EVA. Alternatively, any other suitable material known to those of skill in the art can be used. In general, the materials should be non-reactive to the materials contained inside the concentrate pouch 100. The concentrate pouch 100 can be made from a flexible material formed from two pieces where the pouch side 106 can be welded to another pouch side (not shown). The pouches and/or containers can also be semi-flexible, semi-rigid, or rigid. The pouches and/or containers can be fabricated from any suitable process known to those of ordinary skill. One of ordinary skill will understand that the pouch can be made from any suitable material depending on any desired manufacturing, usage, and size constraints.

Figure 2:
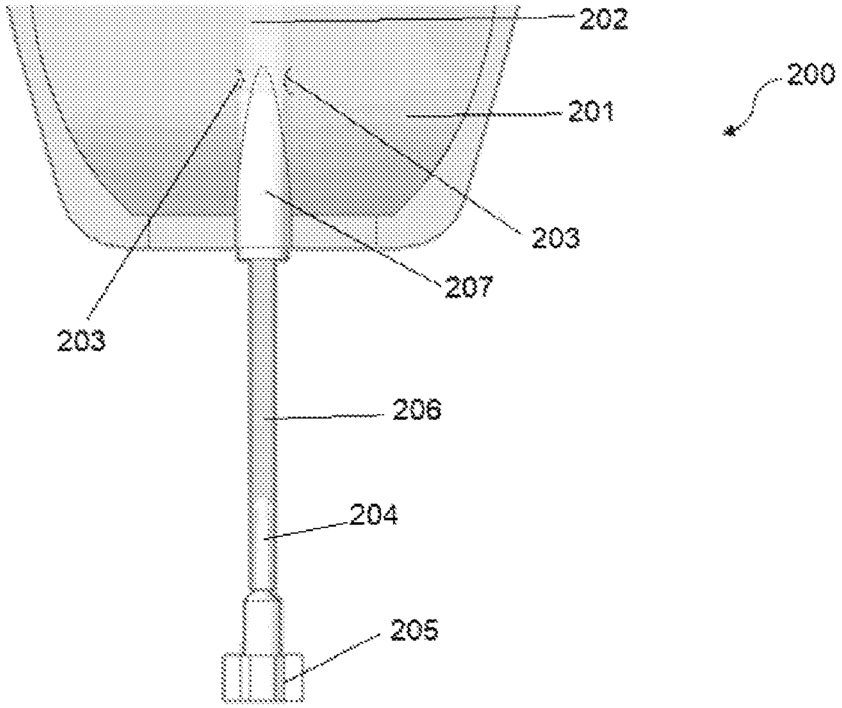
FIG. 2 illustrates a concentrate pouch standing up alone having a threaded connector and a protective cap.

FIG. 2 illustrates a single concentrate pouch 200 standing upright with a protective cap 205. The protective cap 205 can be connected to an external section 206 of fluid tube 202 at section 204. The protective cap 205 can be connected by any means suitable for connecting and disconnecting the protective cap 205 such as a thread, snap-connection, or luer connection. The protective cap 205 can be used when transporting the concentrate pouch 200. In an alternative embodiment, the protective cap 205 can be part of a peritoneal dialysis fluid generation system (not shown) wherein a user first unscrews a cap (not shown) from the section 204, which is threaded, and then screws the threaded protective cap 205 to section 204 to form a fluid connection from the peritoneal dialysate fluid generation system to the concentrate pouch 205. In other embodiments, the protective cap 205 can be simply removed when the concentrate pouch 200 is connected to a fluid line or fluid generation system. Alternatively, the protective cap 205 can be integral to the external section 206. The protective cap 205 can be sterile or non-sterile depending on the desired connection requirement. The external section 206 of the fluid tube 202 can direct fluid to and from the concentrate pouch 200. The external section 206 of the fluid tube 202 can be connected to venturi 207 of the fluid tube 202. The venturi 207 can generate a pressure drop at or around one or more suction port 203. The suction port 203 can be positioned anywhere fluid tube 202 where a pressure drop results from the venturi effect. The suction port 203 can be positioned at or near the bottom so that material falls to at or nearest the lowest point of the concentrate pouch 200 in an upright position. As described, the venturi can speed dissolution of solids inside the pouch body 201 and to help generate a homogenous solution. Although shown as substantially flat in FIG. 2, the interior walls of the concentrate pouch body 201 can include an inclination, similar to that shown in FIGS. 1A-B. Alternatively, the concentrate body 201 can be formed into a funnel-shape.

In certain embodiments, the concentrate pouch 200 can be a stand up pouch. For example, protective cap 205 can have a substantially flat bottom and a large enough diameter to allow the concentrate pouch 200 to remain erect or upright without any additional components supporting the concentrate pouch 200. Alternative components, such as supports (not shown) can also be included to allow the concentrate pouch 200 to stand upright.

Figure 3:
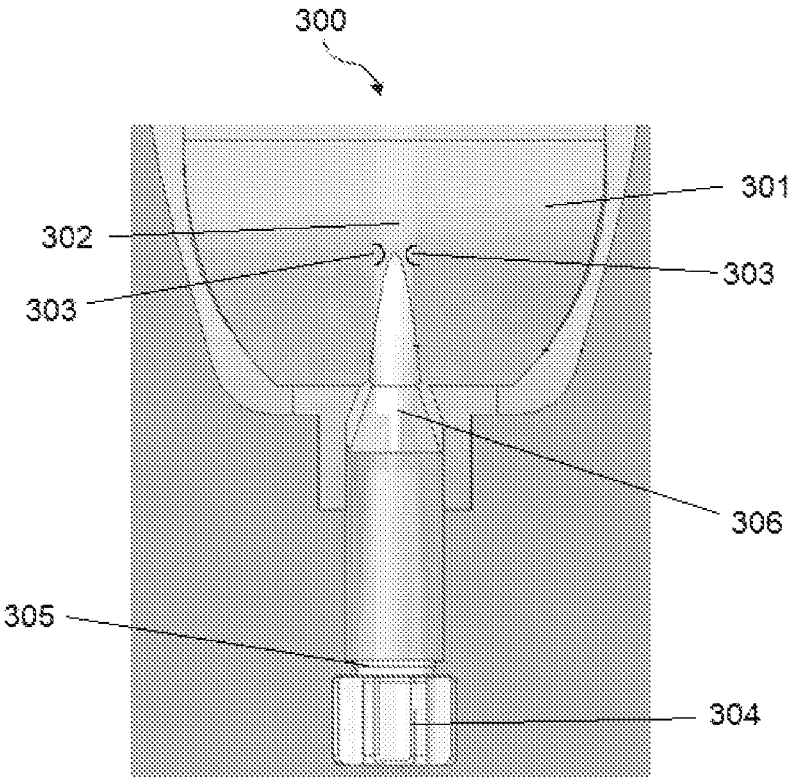
FIG. 3 illustrates a concentrate pouch having a rigid integrated connector and a removable cap flap.

FIG. 3 illustrates a single concentrate pouch 300 standing upright having a rigid integrated connector 300 with a removable cap 304. The removable cap 304 can initially cover connector 305 on the concentrate pouch 300. For use, a user can remove or open removable cap 304 and connect the pouch connectors 305 to a connector on a peritoneal dialysis fluid generation system (not shown). A fluid line of the peritoneal dialysis fluid generation system can connect to fluid tube 302 of the concentrate pouch 300 via connector 305. Fluid can then flow into a constriction 306 that creates a high velocity, low pressure area. As fluid exits constriction 306 a pressure drop can create a vacuum. The fluid tube 302 can include at least one suction port 303 after fluid exits constriction 306 to speed dissolution of solids inside the pouch body 301 and help generate a homogenous solution. Although shown as two suction ports 303 in FIG. 3, the fluid tube 302 can include more suction ports, including between 1 and 6 or more suction ports. Although shown as substantially flat, the pouch body 301 can include an inclination at the bottom of the pouch body 301 to improve dissolution of solids and generate a homogeneous concentrate solution. The bottom of the pouch body 301 can also be formed into a conical or funnel shape. The fluid tube 302 can extend for any length in the interior of the pouch body 301.

Figure 4:
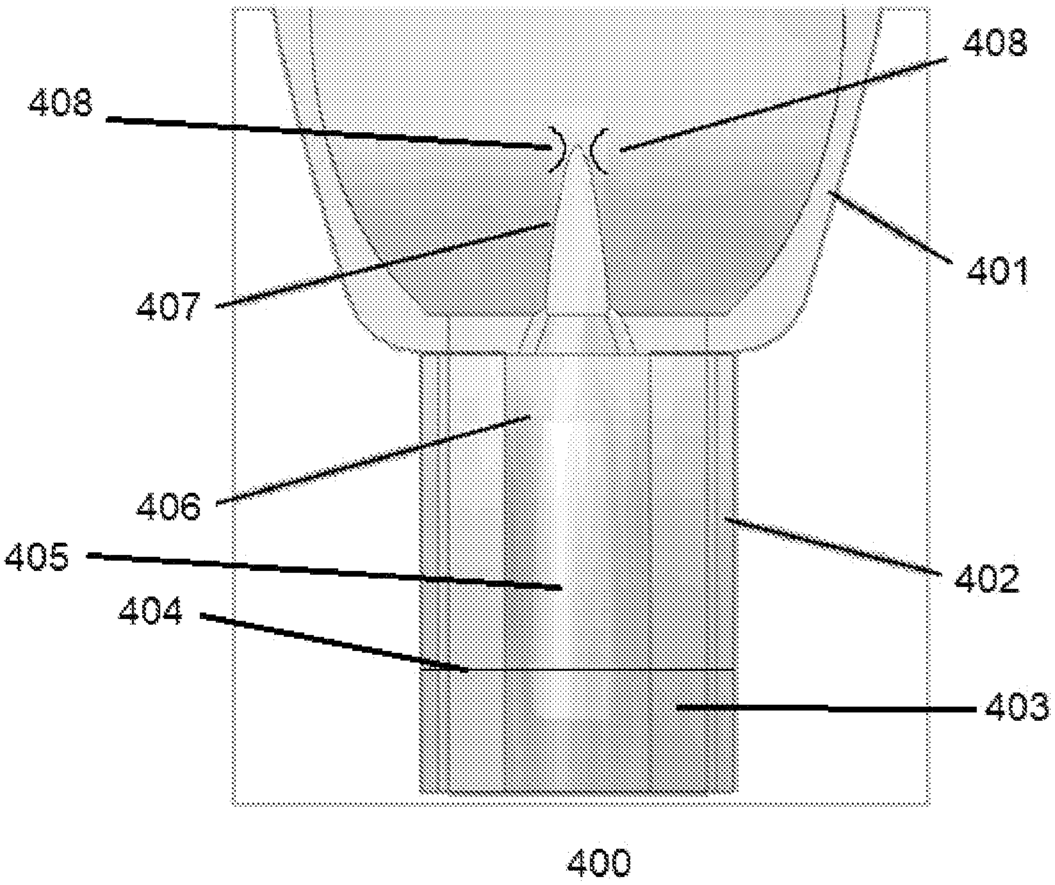
FIG. 4 illustrates a concentrate pouch having a rigid connector and a peelable bottom portion.

FIG. 4 illustrates a single concentrate pouch 400 positioned upright having a rigid fluid connector 405 positioned at the bottom of the concentrate pouch 400 and a peelable bottom portion 403 covering an open end of the pouch 400 The concentrate pouch 400 can include an external layer 402, the bottom of which is a peelable portion 403, which can be peeled away at a line 404. Once peeled, the rigid fluid connector 405 can connect to a complimentary connector (not shown) on a peritoneal dialysis fluid generation system to provide a fluid communication. A fluid line (not shown) of the peritoneal dialysis fluid generation system can be fluidly connected to a tube path 406 of the rigid fluid connector 405. The tube path 406 can have a construction 407 to create an area of high fluid velocity and low pressure. Fluid exiting the constriction 407 can experience a pressure drop. One or more suction ports 408 can vacuum any material or fluid into the fluid path to speed dissolution of solids inside the pouch body 401. The pouch body 401 can include an inclination at the bottom of the pouch body 401 to improve dissolution of solids. Alternatively, the bottom of the pouch body 401 can be in a funnel or conical form to encourage material to collect at the bottom of the pouch body 401.

Figure 5:
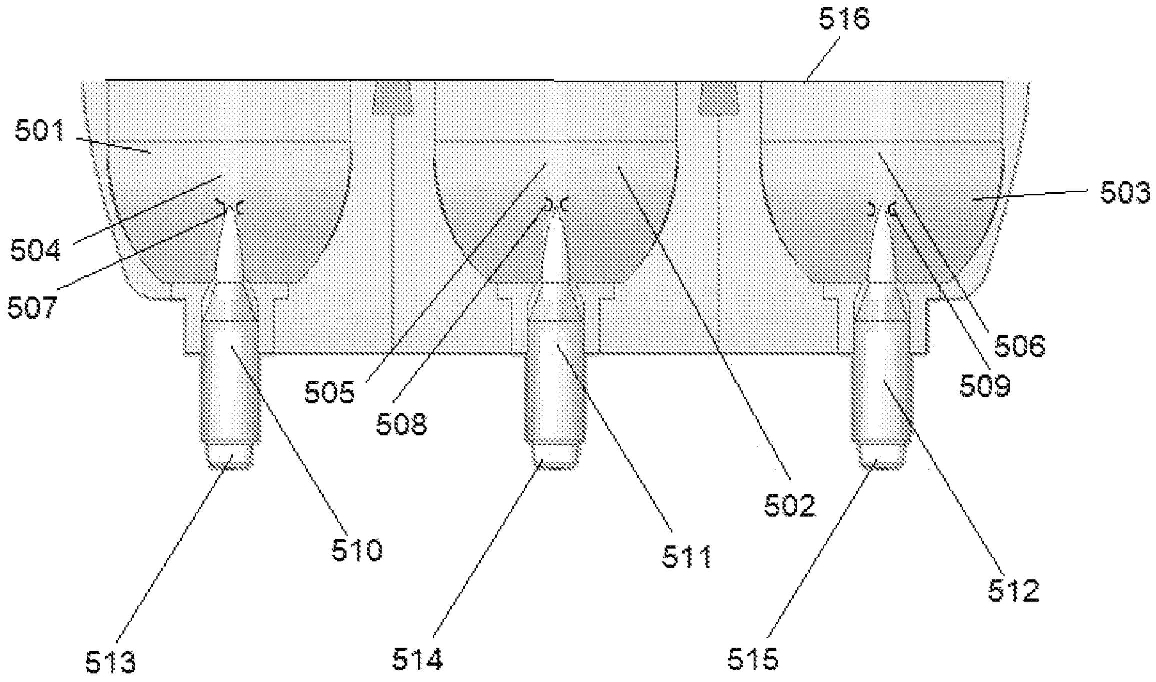
FIG. 5 illustrates multiple concentrate pouches configuration used to generate a peritoneal dialysate.

FIG. 5 illustrates a system using concentrate pouch 501, concentrate pouch 502, and concentrate pouch 503 in an upright orientation. Although shown as three concentrate pouches in FIG. 5, one of skill in the art will understand that any number of concentrate pouches can be used depending on the needs of the system and user. For example, a system requiring two different components that must be dissolved separately can contain a series of two pouches, while a system requiring four or more different components that must be dissolved separately can contain a series of four or more pouches. As illustrated in FIG. 5, concentrate pouch 501, concentrate pouch 502, and concentrate pouch 503 can be connected together by welding or by any suitable structure or component such as a rigid frame. The pouches can be formed into a horizontal line 516 or any suitable configuration. The concentrate pouch 501, concentrate pouch 502, and concentrate pouch 503 can be connected together directly at the sides or any other portion of the concentrate pouch 501, concentrate pouch 502, and concentrate pouch 503. The one or more concentrate pouches of the invention need not be connected, and can instead be separate non-connected pouches.

Each of the concentrate pouch 501, concentrate pouch 502, and concentrate pouch 503 can include a fluid tube 504, fluid tube 505, and fluid 506, respectively, to draw fluid into and out of the respective concentrate pouch 501, concentrate pouch 502, and concentrate pouch 503. As described, each fluid tube 504, fluid tube 505, and fluid 506 can include an integrated venturi system and one or more suction port 507, suction port 508, and suction port 509, respectively. The concentrate pouch 501, concentrate pouch 502, and concentrate pouch 503 can connect to a peritoneal dialysis fluid generation system by any means, including the methods illustrated in FIGS. 2-4. In certain embodiments, the external portion 510, external portion 511, and external portion 512 of the respective fluid tube 504, fluid tube 505, and fluid tube 506 can fluidly connect to fluid lines of the peritoneal dialysis generation system through connector 513, connector 514, and connector 515, respectively.

Water can be added to each of the concentrate pouch 501, concentrate pouch 502, and concentrate pouch 503, dissolving solid or liquid material or diluting a liquid material or solution in the pouch bodies. In certain embodiments, a water purification system can be included in the peritoneal dialysis fluid generation system to purify an incoming water stream prior to pumping the water into the concentrate pouch 501, concentrate pouch 502, and concentrate pouch 503. Alternatively, the concentrate pouch 501, concentrate pouch 502, and concentrate pouch 503 can be fluidly connected to a purified water source. Once the material inside each of concentrate pouch 501, concentrate pouch 502, and concentrate pouch 503 is dissolved or diluted to a specified concentration, concentrate can be pumped out of each of the concentrate pouch 501, concentrate pouch 502, and concentrate pouch 503 to a mixing container, and integrated peritoneal dialysis cycler, or to a storage reservoir. The amounts of each concentrate added from each of the concentrate pouch 501, concentrate pouch 502, and concentrate pouch 503 can be varied to arrive at a predetermined dialysate formulation. A control system (not shown) can be included to control the generation of peritoneal dialysis fluid from the concentrates. The control system can be programmed to pump a specified amount of water into each of concentrate pouch 501, concentrate pouch 502, and concentrate pouch 503 to generate concentrates having specified concentrations. The control system can then operate one or more valves and pumps (not shown) to pump the concentrates out of the concentrate pouches and into the peritoneal dialysis fluid generation system, generating a peritoneal dialysis fluid having specified concentrations of each of the components.

Figure 6A:
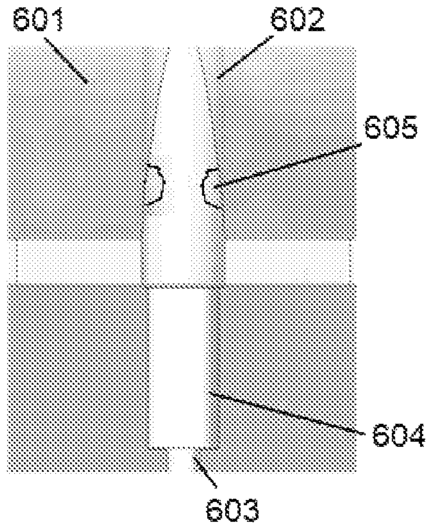
FIGS. 6A-F illustrate close up views of a concentrate pouch and integrated Venturi.
Figure 6B:
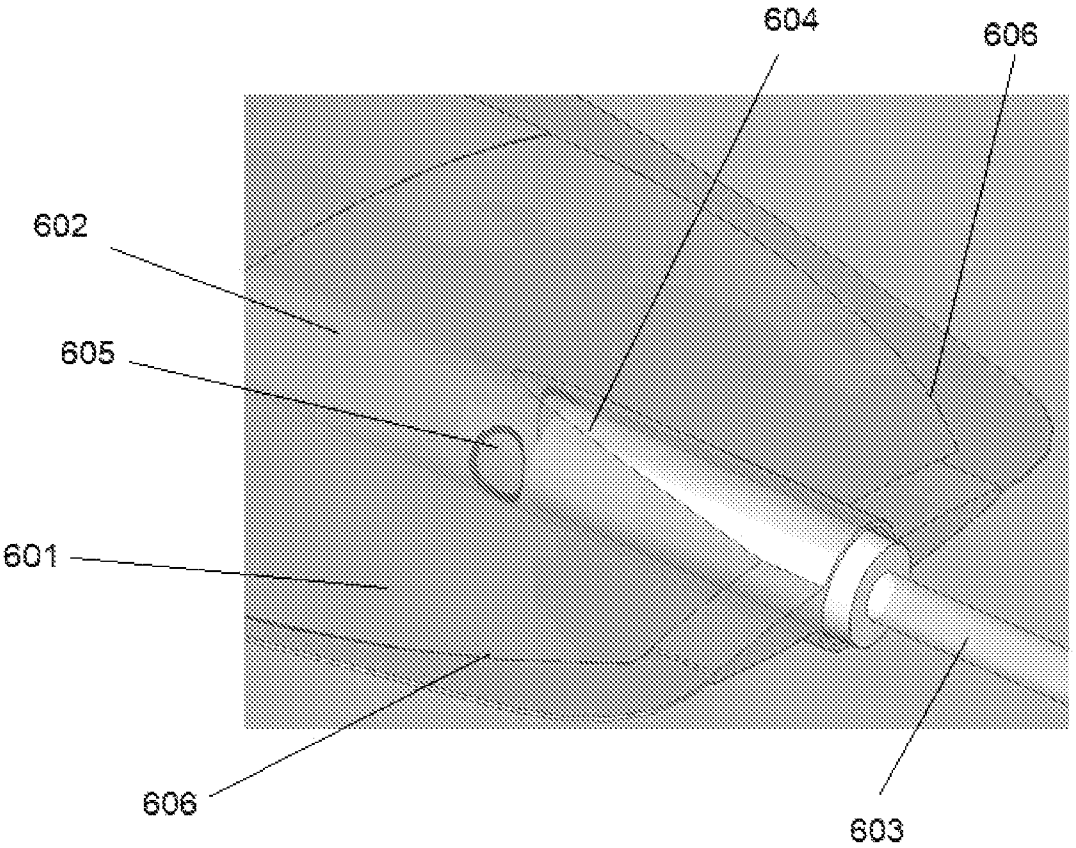
Figure 6C:
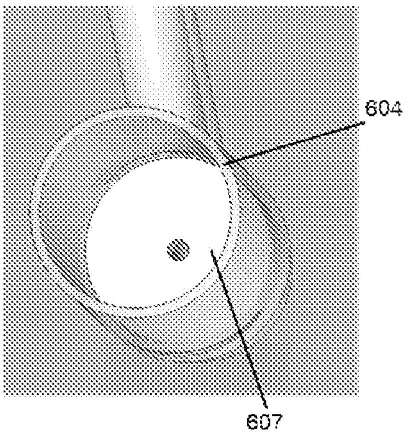
Figure 6D:
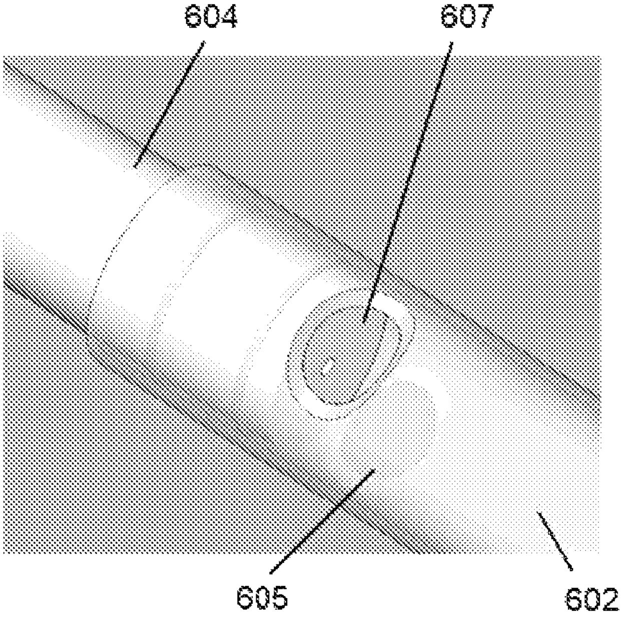
Figure 6E:
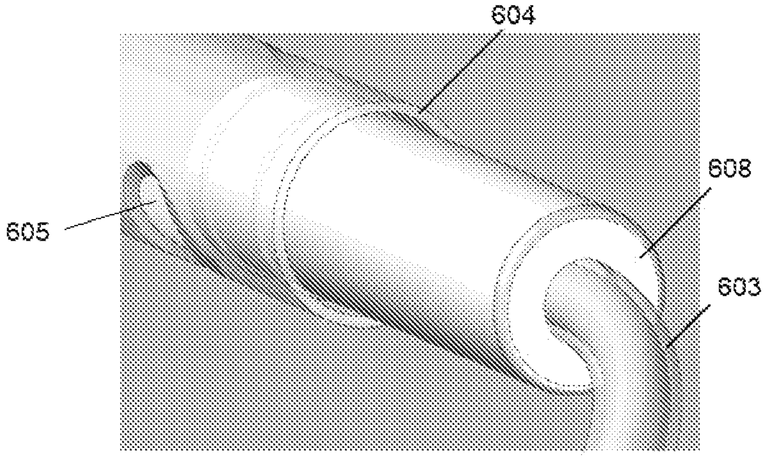
Figure 6F:
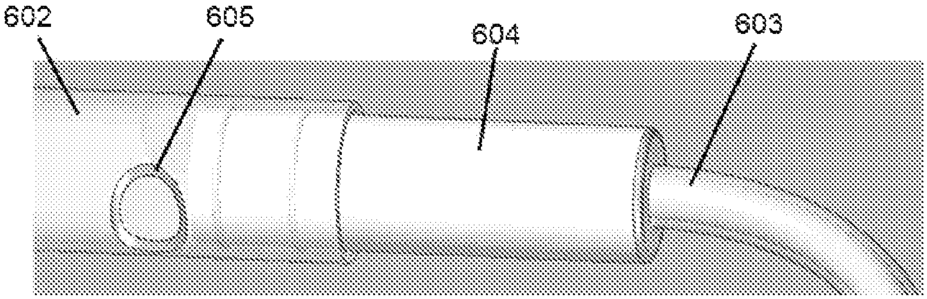

FIG. 6A shows one non-limiting embodiment of close up view of an interior 601 of a concentrate pouch. The interior 601 of the concentrate pouch is in fluid connection to an interior section 602 of a fluid tube. The exterior section 603 of the fluid tube is outside the concentrate pouch. The exterior section 603 can connect to a fluid line of a peritoneal dialysis fluid generation system. The fluid tube can include a venturi section 604 and one or more suction port 605 downstream of the venturi section 604 inside the interior 601 of the concentrate pouch. FIG. 6B shows the venturi section 604 that can contain a constriction (not shown) wherein the exterior section 603 of the fluid tube can be inserted into the bottom of the venturi section 604. The interior section 602 of the fluid tube can be inserted into the top of the venturi section 604. The interior portion 602 and the exterior section 603 of the fluid tube can be formed as part of, and made integral, or inserted into venturi section 604. Any suitable mechanism or arrangement can be used to connect the interior portion 602 and the exterior section 603 to the venturi section 604. FIG. 6C show a cutaway, top perspective of the interior section 602 of the fluid tube. The interior cross section 607 can have a larger area as defined by circumference of the top of the venturi body 604 as compared to a fluid exiting the venturi section 604 into the interior portion 602 of the fluid tube. FIG. 6D is a side perspective showing one or more suction port 605 downstream of venturi section 604 in interior section 602 of the fluid tube. The interior cross section 607 has an area of low pressure which can create a vacuum to suck in material and fluids into the fluid tube via suction port 605. FIG. 6E shows a first diameter 608 of the venturi section 604. Fluid enters the bottom of the venturi section 604 via the exterior section 603 of the fluid tube. Once exiting the venturi section 604, fluid can be mixed with material and fluids being sucked in the fluid tube via suction port 605.

The smaller and larger diameters of the venturi system can be any size capable of generating the required fluid pressure differential. In certain embodiments, the diameter of the venturi section 604 can be up to 5 mm. The fluid tube can have a diameter of between 2-6 mm around the suction ports 605. One or more suction ports 605 can be included, in certain embodiments the number of suction ports 605, and can range between two and six. The diameter of a constriction inside venturi section 604 can range from about 1 mm, while the larger diameter can be about 4 mm. The diameter of the suction port 605 can be around 5 mm. One of ordinary skill in the art can adjust the diameters of any section of the venturi and the diameters of the suction ports to obtain a suitable dissolution under a set of specified conditions. Moreover, the length of the tube inside the interior of the concentrate pouch can be any suitable length. One set of non-limiting parameters can include flow speed, dissolution time, pressure, and temperature.

Experiments were conducted and show that without a venturi system, sodium bicarbonate in a concentrate pouch did not dissolve in less than 10 minutes at a flow rate of 60 ml/min into the concentrate pouch. However, using a venturi system and a water inlet temperature of 48° C., the sodium bicarbonate was completely dissolved in 2.24 minutes providing a final solution temperature of 45° C. Table 1 shows results for a similar experiment using dextrose in a concentrate pouch without a venturi system. Although dissolution tests are influenced by the final concentration, temperature, and other parameters, the experiments show that the venturi system does speed dissolution under the conditions tested.

TABLE 1

| Time to Dissolve/ Mix (min) | Temperature after Dissolution/Mixing (° C.) |
|---|---|
| 130 | 24.5 |
| 45 | 34.6 |
| 30 | 40 |

As shown in Table 1, the dextrose took longer to dissolve or mix at lower temperatures. Without a venturi system, at 24.5° C., the dextrose took 130 minutes to dissolve, at 34.6° C. the dextrose took 45 minutes to dissolve and at 40° C. the dextrose took 30 minutes to dissolve. However, when using a venturi system, the dextrose was dissolved in 4 minutes at 49° C. The venturi system significantly reduced the time of dissolution for all possible powders tested.

As described, peritoneal dialysis fluid can be generated using one or more concentrate pouches. Table 2 provides non-limiting examples of combinations and sizes of pouches that can be used. One of skill in the art will understand that alternative arrangements of materials across one or more oncentrate pouches can be included, and Table 2 is provided for illustrative purposes only.

TABLE 2

| Combination # | Components | Solution volume [L] | Liquid/ powder form |
|---|---|---|---|
| 1 | Dextrose | 2 | Solid |
| | MgCl2 + CaCl2 + NaLac + NaCl | 1 | Solid |
| | Bicarbonate | 1 | Solid |
| 2 | Dextrose | 2 | Solid |
| | MgCl2 + CaCl2 + NaLac + NaCl | 0.5 | Liquid |
| | Bicarbonate | 1 | Solid |
| 3 | Dextrose | 2 | Solid |
| | MeCl2 + CaCl2 + NaLac | 0.5 | Solid |
| | NaBic + NaCl | 1 | Solid |
| 4 | Dextrose | 2 | Solid |
| | MgCl2 + CaCl2 + NaLac | 0.5 | Liquid |
| | NaBic + NaCl | 1 | Solid |
| 5 | Dextrose | 2 | Solid |
| | MeCl2 + CaCl2 | 0.25 | Solid |
| | NaBic + NaCl + NaLac | 1 | Solid |

TABLE 2-continued

| Combination # | Components | Solution volume [L] | Liquid/ powder form |
|---|---|---|---|
| 6 | Dextrose | 2 | Solid |
| | MgCl2 + CaCl2 | 0.25 | Solid |
| | NaBic + NaCl + NaLac | 1 | Liquid |
| 7 | Dextrose | 2 | Solid |
| | MgCl2 + CaCl2 + NaLac | 0.5 | Solid |
| | NaCl | 0.5 | Solid |
| 8 | Dextrose | 2 | Solid |
| | MgCl2 + CaCl2 + NaLac | 0.5 | Liquid |
| | NaCl | 0.5 | Solid |
| 9 | Dextrose | 2 | Solid |
| | MgCl2 + CaCl2 | 0.25 | Solid |
| | NaCl + NaLac | 0.5 | Solid |
| 10 | Dextrose | 2 | Solid |
| | MgCl2 + CaCl2 | 0.25 | Solid |
| | NaCl + NaLac | 0.5 | Liquid |

The peritoneal dialysis fluid generated using the concentrate pouches can include sodium chloride, sodium lactate, magnesium chloride, calcium chloride, dextrose, and optionally sodium bicarbonate. However, in certain embodiments, the lactate can be eliminated and only sodium bicarbonate used, or the sodium bicarbonate eliminated and only sodium lactate. In each of the combinations listed in Table 2, dextrose is provided in a concentrate pouch without any other components. Providing dextrose without additional components allows for the dextrose concentration of the resulting peritoneal dialysis fluid to be set independently of the sodium, magnesium, calcium, or buffer concentrations, allowing therapy to be customized based on the medical prescription. However, in certain embodiments, the dextrose can be included in a single concentrate pouch with one or more additional components. Other osmotic agents can be used in addition to, or in place of dextrose. For example, icodextrin or other polydextrin can be used as an osmotic agent for generating peritoneal dialysis fluid.

In certain embodiments, the magnesium chloride and calcium chloride can be provided separately from the sodium bicarbonate. Bicarbonate can be separated from the magnesium and calcium to avoid precipitation. While bicarbonate can be separated from the magnesium and calcium, any 2 or more concentrate containers can be used with the other components in any arrangement. For example, in combination 7 of Table 2, the magnesium and calcium ions are included with sodium lactate. In combination 5 of Table 2, the sodium lactate is separated from the magnesium and calcium. Sodium chloride can be included in any concentrate pouch. When both bicarbonate and lactate are used the bicarbonate and lactate may be in the same concentrate pouch, as shown in combination 5, but the bicarbonate can remain separate from the magnesium and calcium. Each of the components can be provided in either solid or liquid form. The actual combination used can depend on the needs of the user.

One skilled in the art will understand that various combinations and/or modifications and variations can be made in the described systems and methods depending upon the specific needs for operation. Various aspects disclosed herein may be combined in different combinations than the combinations specifically presented in the description and accompanying drawings. Moreover, features illustrated or described as being part of an aspect of the disclosure may be used in the aspect of the disclosure, either alone or in combination, or follow a preferred arrangement of one or more of the described elements. Depending on the example, certain acts or events of any of the processes or methods described herein may be performed in a different sequence, may be added, merged, or left out altogether (e.g., certain described acts or events may not be necessary to carry out the techniques). In addition, while certain aspects of this disclosure are described as performed by a single module or unit for purposes of clarity, the techniques of this disclosure may be performed by a combination of units or modules associated with, for example, a medical device.

The invention claimed is:

1. A concentrate pouch, comprising:

a fluid inlet positioned at a bottom portion of the concentrate pouch, the fluid inlet comprises a venturi tube extending upwardly into an interior portion of the concentrate pouch, the venturi tube comprising:

a first section distal to the interior portion of the concentrate pouch, the first section having a first diameter, wherein the interior portion is configured to house an initial material;

a second section distal to the first section and proximal to the interior portion of the concentrate pouch, the second section having a second diameter smaller than the first diameter forming a constriction, and a third section distal to the second section and extending inwardly into the interior portion of the concentrate pouch, the third section having a third diameter larger than the second diameter, and having a suction port at or about a floor of the interior portion of the concentrate pouch, the suction port exposing an interior of the venturi tube to the interior portion of the concentrate pouch, wherein the venturi tube defines a flow path for a fluid, the flow path comprising the first section, the second section, and the third section, and wherein the venturi tube is configured to cause the initial material to suction through the suction port into the interior portion of the venturi tube to mix with the fluid in the flow path, and wherein the first diameter of the first section or the third diameter of the third section is four times the second diameter of the second section.

2. The concentrate pouch of claim 1, wherein the initial material comprises a solid material.

3. The concentrate pouch of claim 1, wherein the concentrate pouch is constructed of a flexible material.

4. The concentrate pouch of claim 1, wherein the concentrate pouch is constructed of a flexible material and a stand up pouch.

5. The concentrate pouch of claim 1, wherein the floor of the concentrate pouch inwardly tapers towards the fluid inlet.

6. The concentrate pouch of claim 1, the venturi tube extending upwardly from a bottom of the concentrate pouch towards a top of the concentrate pouch.

7. A system comprising:

one or more concentrate pouches of claim 1, fluidly connected to a peritoneal dialysis fluid generation flow path; and a control system programmed to:

pump water into the one or more concentrate pouches to generate a concentrate; and pump a concentrate from the one or more concentrate pouches into the peritoneal dialysis fluid generation flow path and into a mixing container.

8. The system of claim 7, further comprising a water source fluidly connectable to the one or more concentrate pouches.

9. The system of claim 7, wherein the one or more concentrate pouches comprise a concentrate pouch containing dextrose, icodextrin, or a polydextrin, a concentrate pouch containing magnesium, calcium and sodium lactate, and a concentrate pouch containing sodium bicarbonate and sodium chloride.

10. The system of claim 7, wherein the one or more concentrate pouches comprise a concentrate pouch containing dextrose, icodextrin, or a polydextrin, a concentrate pouch containing magnesium and calcium, and a concentrate pouch containing sodium bicarbonate, sodium chloride, and sodium lactate.

11. The system of claim 7, wherein the one or more concentrate pouches comprise a concentrate pouch containing dextrose, icodextrin, or a polydextrin, a concentrate pouch containing magnesium, calcium, and sodium lactate, and a concentrate pouch containing sodium chloride.

12. The system of claim 7, wherein the one or more concentrate pouches comprise a concentrate pouch containing dextrose, icodextrin, or a polydextrin, a concentrate pouch containing magnesium and calcium, and a concentrate pouch containing sodium chloride and sodium lactate.

13. The system of claim 7, wherein the initial material of at least one of the one or more concentrate pouches comprises a solid substance.

14. The system of claim 7, wherein the initial material of at least one of the one or more concentrate pouches comprises a liquid or aqueous substance.

15. The system of claim 7, wherein the control system is programmed to pump an amount of water into the one or more concentrate pouches to generate a concentrate; and to pump an amount of water into the one or more concentrate pouches to completely dissolve materials within the one or more concentrate pouches.

16. The system of claim 7, wherein at least one of the one or more concentrate pouches is a stand up pouch.

17. A method, comprising the steps of:

pumping water into one or more of the concentrate pouch of claim 1 via the fluid flow path;

dissolving a material within the one or more concentrate pouches to generate a concentrate in each of the one or more concentrate pouches; and pumping the concentrate out of each of the one or more concentrate pouches.

18. The method of claim 17, further comprising the step of pumping the concentrate from each concentrate pouch of the one or more concentrate pouches to a mixing container.

19. The method of claim 17, wherein the one or more concentrate pouches comprise a concentrate pouch containing dextrose, icodextrin, or a polydextrin, a concentrate pouch containing magnesium, calcium and sodium lactate, and a concentrate pouch containing sodium bicarbonate and sodium chloride.

* * * * *